United States Patent
Platts-Mills et al.

(10) Patent No.: US 8,450,068 B2
(45) Date of Patent: May 28, 2013

(54) IGE ANTIBODIES TO CHIMERIC OR HUMANIZED IGG THERAPEUTIC MONOCLONAL ANTIBODIES AS A SCREENING TEST FOR ANAPHYLAXIS

(75) Inventors: Thomas A. E. Platts-Mills, Charlottesville, VA (US); Tina Hatley Merritt, Bentonville, AR (US)

(73) Assignee: University of Virginia Patent Foundation, Charlottesville, VA (US)

( * ) Notice: Subject to any disclaimer, the term of this patent is extended or adjusted under 35 U.S.C. 154(b) by 646 days.

(21) Appl. No.: 12/527,255

(22) PCT Filed: Feb. 15, 2008

(86) PCT No.: PCT/US2008/054113
§ 371 (c)(1),
(2), (4) Date: Aug. 14, 2009

(87) PCT Pub. No.: WO2008/101177
PCT Pub. Date: Aug. 21, 2008

(65) Prior Publication Data
US 2010/0120058 A1  May 13, 2010

Related U.S. Application Data

(60) Provisional application No. 60/901,725, filed on Feb. 16, 2007, provisional application No. 60/963,597, filed on Aug. 6, 2007.

(51) Int. Cl.
*G01N 33/53* (2006.01)

(52) U.S. Cl.
USPC ......... 435/7.1; 435/7.92; 435/7.93; 435/7.94; 435/7.95; 424/805; 424/810

(58) Field of Classification Search
None
See application file for complete search history.

(56) References Cited

U.S. PATENT DOCUMENTS

| | | |
|---|---|---|
| 5,785,966 A | 7/1998 | Coles et al. |
| 6,096,725 A | 8/2000 | Simon et al. |
| 6,572,867 B1 | 6/2003 | Schwarz et al. |
| 2004/0052785 A1* | 3/2004 | Goodman et al. ......... 424/143.1 |

FOREIGN PATENT DOCUMENTS

| | | |
|---|---|---|
| WO | WO 9640210 A1 * | 12/1996 |
| WO | WO-2008101177 A2 | 8/2008 |
| WO | WO-2008101177 A3 | 8/2008 |

OTHER PUBLICATIONS

Kuby J., Immunology, 1992, W.H. Freeman and Co., p. 125.*
Sheeley et al., Anal Biochem. Apr. 5, 1997;247(1):102-10.*
Erwin et al., J Allergy Clin Immunol. May 2005;115(5):1029-35.*
Thomas M., Clin J Oncol Nurs. Jun. 2005;9(3):332-8.*
Janeway et al., Immunobiology, 3rd edition, Garland Publishing, 1997, 11:1-11:3.*
Jin et al., J Allergy Clin Immunol. Jan. 2008;121(1):185-190.e2. Epub Sep. 19, 2007.*
"International Application Serial No. PCT/US2008/054113, International Preliminary Report on Patentability mailed Aug. 19, 2009", 4 pgs.
"International Application Serial No. PCT/US2008/054113, International Search Report and Written Opinion mailed Nov. 12, 2008", 5 pgs.
Chung, C. H, et al., "Cetuximab-induced anaphylaxis and IgE specific for galactose-alpha-1,3-galactose", N Engl J Med., 358(11), (Mar. 13, 2008), 1109-17.
Goldstein, N. I, et al., "Biological efficacy of a chimeric antibody to the epidermal growth factor receptor in a human tumor xenograft model", Clin Cancer Res., 1(11), (Nov. 1995), 1311-8.
Kershaw, M. H, et al., "Tumor-specific IgE-mediated inhibition of human colorectal carcinoma xenograft growth", Oncol Res., 10(3), (1998), 133-42.
O'Neil, B. H, et al., "High incidence of cetuximab-related infusion reactions in Tennessee and North Carolina and the association with atopic history", Journal of Clinical Oncology, 25(24), (Aug. 20, 2007), 3644-3648.

\* cited by examiner

*Primary Examiner* — Michael Szperka
(74) *Attorney, Agent, or Firm* — Schwegman Lundberg & Woessner, P.A.

(57) ABSTRACT

The present invention provides an assay for detecting serum IgE antibody levels to cetuximab and to other proteins. The present invention further provides a method for predicting whether a subject will respond adversely to cetuximab treatment. The present further provides a method for detecting sensitivity to compounds comprising galactose-alpha-1,3-galactose.

14 Claims, 2 Drawing Sheets

IGE ANTIBODIES TO CHIMERIC OR HUMANIZED IGG THERAPEUTIC MONOCLONAL ANTIBODIES AS A SCREENING TEST FOR ANAPHYLAXIS

CROSS REFERENCE TO RELATED APPLICATIONS

This application is a national stage filing of International Application No. PCT/US2008/054113, filed Feb. 15. 2008, which is entitled to priority pursuant to 35 U.S.C. § 119(e) to U.S. provisional patent application nos. 60/901,725, filed on Feb. 16, 2007 and 60/963,597, filed on Aug. 6, 2007. The entire disclosures of the afore-mentioned patent applications are incorporated herein by reference.

STATEMENT REGARDING FEDERALLY SPONSORED RESEARCH OR DEVELOPMENT

This invention was made with government support under Grant No. AI-20565 awarded by the National Institutes of Health. The United States Government has certain rights in the invention.

FIELD OF THE INVENTION

The present invention relates generally to methods for determining whether a subject treated with cetuximab will have an adverse reaction to the treatment.

BACKGROUND

ERBITUX™ (Cetuximab) is a recombinant, human/mouse chimeric monoclonal antibody manufactured by ImClone Systems Incorporated and distributed and marketed by Bristol-Myers Squibb Company. 3% of patients receiving ERBITUX™ (Cetuximab) have an adverse reaction to the drug. 90% of the severe reactions are associated with initial drug infusion. Adverse reactions include rapid onset of airway obstruction (including anaphylaxis.)

Recombinant monoclonal antibodies (mAb) are playing an increasing role in the management of many diseases including malignancies, inflammatory bowel disease, rheumatoid arthritis, and asthma (1, 2, 3). While these agents are generally well tolerated, hypersensitivity reactions (HSR) occur and can be both rapid and severe (4, 5, 6, 7). Cetuximab, a chimeric (mouse/human) IgG1 mAb against the epidermal growth factor receptor (EGFR) is approved for use in patients with metastatic colorectal cancer (CRC) and head and neck squamous cell carcinoma (HNSCC) (2,6,8,9,10). According to the Drug Product Label, severe HSR to cetuximab occur in 3% of cases. However, higher rates and clusters of cases have been reported from North Carolina, Arkansas, Missouri, Virginia and Tennessee (6,9,11). A recent publication reported that 22% of patients treated with cetuximab in Tennessee and North Carolina had severe HSR (11). By contrast, rates of HSR are lower (<1%) in most centers in the northeast. Review of the case reports on HSR to cetuximab revealed that many occurred within minutes of first exposure to the drug and were compatible with IgE mediated anaphylaxis (12,13).

There is a long felt need in the art for methods helpful in predicting whether a subject will react adversely to treatment with a protein such as cetuximab. The present invention satisfies this need.

BRIEF SUMMARY OF THE INVENTION

The present invention encompasses compositions and methods useful for determining if a subject has a predisposition to an adverse reaction to cetuximab. The present invention discloses that subjects susceptible to an adverse reaction to cetuximab have pre-existing IgE antibodies that cross-react with cetuximab (CR-IgE), while subjects who do not have adverse reactions to cetuximab do not have such levels of pre-existing IgE antibodies that cross-react with cetuximab. The presence of these antibodies can therefore serve as a biomarker, the presence of which suggests that the subject has a predisposition or susceptibility to an adverse reaction to cetuximab, particularly the more rapid onset reactions. The present invention further discloses that the subjects are sensitive to the oligosaccharide moiety galactose-alpha-1,3-galactose (alphaGal) on cetuximab. Adverse reactions to cetuximab include, but are not limited to, allergic reactions, difficulty breathing, rapid onset of airway obstruction, rash, itching, low blood pressure, loss of consciousness, HSR, anaphylaxis, and heart attack.

Disclosed herein is the successful development of an assay to measure CR-IgE. This assay utilizes a modification of the ImmunoCAP assay where the solid phase is a streptavidin-activated polymer sponge, which allows high quantities of biotinylated antigens to be bound (14).

Data disclosed herein provide strong evidence that the pre-existing antibodies directed against cetuximab are a cause of the adverse reactions, particularly severe HSR, which has been described in a low percentage of patients receiving cetuximab treatment. The present application further discloses that the CR-IgE that binds to cetuximab specifically bind to an oligosaccharide, galactose-alpha-1,3-galactose (alphaGal), which is present on the Fab portion of the cetuximab heavy chain. They also cross-react with specificity to a range of mammalian proteins, suggesting that the binding is to an epitope such as the galactose-alpha-1,3-galactose moiety. Finally, it is demonstrated herein that there is a high prevalence of CR-IgE in areas of this country where anaphylactic reactions to cetuximab occur.

Quantitative measurements of IgE antibodies to therapeutic monoclonal antibodies using International Units have not been previously described until the present invention. Previous systems, i.e., ELISAs, have very low solid phase binding and are generally considered unreliable for measuring IgE antibodies. The present invention discloses, inter alia, a fast and sensitive method for measuring IgE antibodies, comprising use of an ImmunoCAP assay or a modified ImmunoCAP assay. In one aspect, the IgE antibodies are directed against cetuximab. In one aspect, the greater the level of IgE antibodies cross-reactive with cetuximab detected in a test subject, the greater the predisposition to an adverse reaction to cetuximab. One of ordinary skill in the art will appreciate that any assay which can measure IgE directed against a compound of interest of the invention can be used.

In one embodiment, the present invention provides compositions and methods useful for screening subjects to assess the risks of adverse reactions to cetuximab, particularly the risks of HSR and of anaphylaxis, before treatment with cetuximab. In one aspect, the method provides a test that is highly predictive of HSR. In one aspect, the HSR is severe HSR.

Although cetuximab can be used in the screening assay, other compounds which bind similarly to the same cross-reactive IgE antibodies can be used in the assay instead of cetuximab. For example, as demonstrated herein, the F(ab')$_2$ fragment of cetuximab can be used as well as other compounds comprising a galactose-alpha-1,3-galactose moiety. It is understood that if such a compound is used to detect IgE antibodies that standardization assays can be performed first to normalize the result relative to the use of cetuximab, or to determine cross-reactive IgE antibody levels which are safe before administering a therapeutic molecule comprising the moiety.

Because of the sensitivity and quantitative nature of the assay for measuring cross-reactive IgE antibodies described herein, namely the ImmunoCAP and modified ImmunoCAP assays, the invention encompasses the use of the assays to measure cross-reactive IgE against other compounds known to elicit adverse reactions that might be mediated by IgE, and not just IgE that cross-react with cetuximab.

In one embodiment, the invention provides a method which detects and measures IgE antibodies in a subject that are cross-reactive with cetuximab. In one aspect, the antibodies are present before treatment with cetuximab. In one aspect, the method detects and measures binding to a target compound, such as cetuximab, where the IgE binds a sugar moiety on the compound. In one aspect, the compound is therapeutic antibody. In one aspect, the therapeutic antibody is cetuximab. In one aspect, the sugar moiety is galactose-alpha-1,3-galactose.

In one embodiment, the present invention provides compositions and methods useful for detecting and measuring the amount of cross-reactive IgE antibody to cetuximab that is present in a subject before cetuximab treatment. One of ordinary skill in the art will realize that various techniques can be used to screen serum for cross-reactivity to IgE antibodies directed against cetuximab or sugar moieties attached to cetuximab.

In one aspect, when the levels of cross-reactive IgE antibodies against cetuximab are higher in a test subject relative to the average levels in the general population or to someone not predisposed to an adverse reaction to cetuximab is an indication that the test subject will be hypersensitive to treatment with cetuximab and is susceptible or predisposed to reacting adversely to treatment with cetuximab. One of ordinary skill in the art will appreciate that various means are available to either determine what is an average level of cross-reactive IgE antibodies against cetuximab and will appreciate that controls and standards can be established or utilized to assess whether the subject has levels of cross-reactive IgE antibodies against cetuximab which are higher than normal and can be used to predict whether the subject will be hypersensitive to treatment with cetuximab. In one aspect, the assay can target the oligosaccharide moiety galactose-alpha-1,3-galactose, which is an oligosaccharide moiety on cetuximab, as well as on other proteins.

In one aspect, the level of IgE antibody a sample from a test subject which cross-reacts with cetuximab is selected from the group consisting of at least about 0.1 IU/ml, at least about 0.35 IU/ml, at least about 1.0 IU/ml, at least about 5.0 IU/ml, at least about 10.0 IU/ml, at least about 20.0 IU/ml, at least about 50.0 IU/ml, at least about 100.0 IU/ml, and at least about 150.0 IU/ml. These levels can be correlated with the potential for an adverse reaction. One of ordinary skill in the art will use the identified levels as part of an assessment of the potential of an adverse reaction to cetuximab and whether or not to use cetuximab to treat a subject, such as a subject with colorectal cancer or head and neck squamous cell carcinoma. Other considerations include such things as the age, sex, health, and weight of the subject. The level of cross-reactive IgE in the test subject may be used as part of the analysis when considering alternative or combination treatments, dosages of the therapeutic compound to be administered, the route of administration, etc.

When it is determined that a subject is at risk for an adverse reaction if treated with cetuximab, additional options for consideration include, the subject could be treated with cetuximab which had been prepared without the sugar moiety or with cetuximab from which galactose-alpha-1,3-galactose had been removed, or steps can be taken to avoid the adverse reaction by use of different therapies or means to diminish the adverse reaction.

In one embodiment, the subject is a human.

One of ordinary skill in the art will appreciate that any sample obtained from a subject which contains IgE antibodies can be used. In one aspect, the sample is selected from the group consisting of blood, serum, and plasma.

In one embodiment, an IgE antibody that binds with cetuximab binds with the F(ab')2 fragment of cetuximab. In one aspect, it binds with the moiety galactose-alpha-1,3-galactose on the F(ab')2 fragment of cetuximab.

Assays which are useful for measuring CR-IgE are encompassed by the invention. Useful ligands for binding to and measuring CR-IgE include cetuximab, as well as fragments, homologs, derivatives, and modifications thereof which still bind to the CR-IgE, as well as other molecules comprising the sugar moiety described herein. In one aspect, a fragment of cetuximab useful for the practice of the invention is one which comprises the sugar moiety galactose-alpha-1,3-galactose. Other useful compounds to which the CR-IgE could bind in the assay include other proteins, including allergens, antibodies, monoclonal antibodies, therapeutic antibodies, humanized antibodies, and chimeric antibodies. In one aspect, the CR-IgE binds to a galactose-alpha-1,3-galactose moiety on the other compounds. The assay is therefore useful for identifying compounds comprising a galactose-alpha-1,3-galactose moiety as well as determining if a subject is predisposed to an adverse reaction to a molecule comprising a galactose-alpha-1,3-galactose moiety. One of ordinary skill in the art will appreciate that the assay is useful for other sugar moieties as well.

The present invention further encompasses measuring in a subject the level of IgE antibody against a test compound to determine if the subject has a predisposition to an adverse reaction to that molecule if that compound were administered to that subject or if the subject were to be exposed to that compound other than by direct administration. Such test compounds include, but are not limited to proteins, allergens, antibodies, monoclonal antibodies, therapeutic antibodies, humanized antibodies, and chimeric antibodies (see Table 3 and descriptions of examples such as dog, cat, beef and pork). In one aspect, the compounds are mammalian.

The present invention provides compositions and methods useful for monitoring cross-reactive IgE antibody levels during treatment of a subject with a compound which may cause an adverse reaction. In on embodiment, the compound is cetuximab. Other compounds described herein or which may elicit adverse reactions via an IgE mediated response are also encompassed by this method.

The present invention further provides a kit to perform the assays of the invention.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
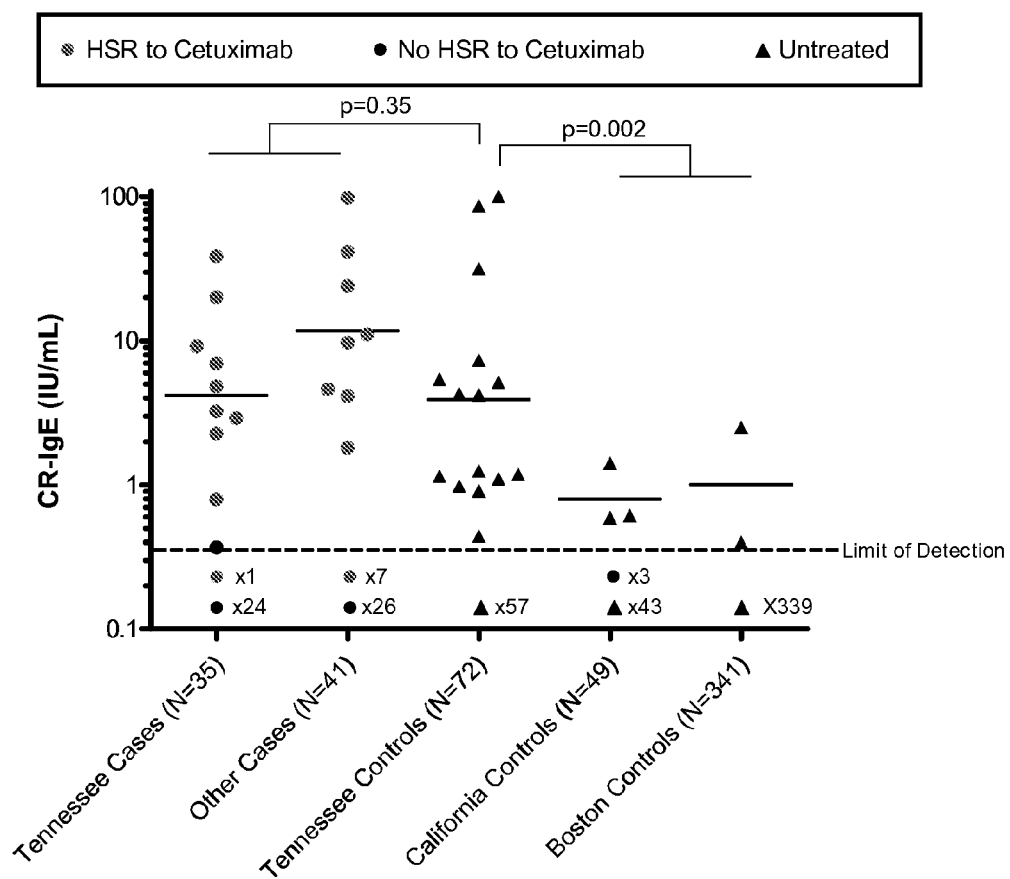
FIG. 1 graphically represents the results of experiments demonstrating that IgE antibodies cross react with cetuximab (CR-IgE) in sera from the four cohorts. Reactions to cetuximab were classified by the treating physicians (HSR to cetuximab ◉; No HSR ●) sera from controls and patients who had not received cetuximab: ▲. The dashed line (- - -) indicates the limit of detection.

Abbreviations and Acronyms
alphaGal—galactose-alpha-1,3-galactose
EGF—epidermal growth factor
EGFR—epidermal growth factor receptor
CHO—chinese hamster ovary
CRC—colorectal cancer
CR-IgE—IgE antibody cross reacting with cetuximab
HNSCC—head and neck squamous cell carcinoma
HSR—hypersensitivity reaction
mAb—monoclonal antibody
NGNA—N-glyconeurominic acid
NMBA—neuromuscular blocking agent
TNF—tumor necrosis factor
VH—immunoglobulin heavy chain variable region
VL—immunoglobulin light chain variable region
Definitions In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "affected cell" refers to a cell of a subject afflicted with a disease, injury, or disorder, which affected cell has an altered phenotype relative to a subject not afflicted with a disease or disorder.

Cells or tissue are "affected" by a disease, injury, or disorder if the cells or tissue have an altered phenotype relative to the same cells or tissue in a subject not afflicted with a disease or disorder.

A disease, condition, or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

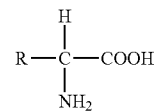

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
H is, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497). "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, the term "biologically active fragments" or "bioactive fragment" of the polypeptides encompasses natural or synthetic portions of the full-length protein that are capable of specific binding to their natural ligand or of performing the function of the protein.

A "compound", as used herein, refers to any type of substance or agent that is commonly considered a chemical, drug, or a candidate for use as a drug, as well as combinations and mixtures of the above. The term also includes other types of molecules, such as proteins, allergens, etc., as described herein.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound," as used herein, refers to any type of substance or agent that is commonly considered a drug, or a candidate for use as a drug, a polypeptide, an isolated nucleic acid, an antibody, or other agent used in the method of the invention, as well as any combination thereof.

The terms "cross-react" and specifically binds" are used interchangeably herein.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly 5 amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCCS' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound or any agent to reduce or impede a described function. Preferably, inhibition is by at least 10%, more preferably by at least 25%, even more preferably by at least 50%, and most preferably, the function is inhibited by at least 75%.

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated."

An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds. Thus, under designated assay (e g , immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity or cross-reactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester, linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term in nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH2OC(O)NR—), a phosphonate linkage, a —CH2-sulfonamide (—CH2—S(O)2NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R2 is selected from the group consisting of C1-C4 alkoxy, and —NR3R4 where R3 and R4 are independently selected from the group consisting of hydrogen and $C_1$-$C_4$ alkyl.

The term "permeability," as used herein, refers to transit of fluid, cell, or debris between or through cells and tissues.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The Willi "purified" does not necessarily indicate that complete purity of the particular molecule has been achieved during the process. A "highly purified" compound as used herein refers to a compound that is greater than 90% pure.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds," as used herein, is meant a compound which recognizes and binds a specific protein or molecule, but does not substantially recognize or bind other molecules in a sample, or it means binding between two or more proteins as in part of a cellular regulatory process, where said proteins do not substantially recognize or bind other proteins in a sample.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured. A "standard sample" is, for example, one with known amounts of a compound of interest. When it is said that a test sample has a higher level of a compound than that in a standard sample it is meant that it is higher based on normalizing the data such that the level in the test sample is determined to be higher than that found in a sample from a normal subject, etc.

By the term "susceptible to an adverse reaction to cetuximab," as used herein, is meant a subject who has preexisting IgE antibodies capable of cross-reacting or binding with cetuximab, which in turn may result in an adverse reaction if cetuximab is administered to the subject. The presence of the cross-reactive antibodies to cetuximab in a subject would be an indication that the subject would have an adverse reaction if treated with cetuximab. Therefore, the term "is susceptible" also includes those subjects who may be susceptible to an adverse reaction to cetuximab because of increased levels of the IgE antibody relative to levels in subjects who have not, or who are not, susceptible to an adverse reaction to cetuximab, particularly a severe adverse reaction.

The tem "susceptible to an adverse reaction to cetuximab" is used interchangeably with the term "a predisposition to an adverse reaction to cetuximab."

A "subject" of diagnosis or treatment is a mammal, including a human.

A "test" subject is a subject being treated or tested.

A "therapeutic antibody," as used herein, refers to antibodies, including monoclonal antibodies or fragments or homologs of antibodies, which are administered to a subject to treat or prevent a disease or disorder in the subject.

As used herein, the term "treating" includes prophylaxis of the specific disease, disorder, or condition, or alleviation of the symptoms associated with a specific disease, disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Embodiments

Although the present invention is useful for determining whether a subject is susceptible to a quick adverse reaction to cetuximab, the present invention may also be useful for determining if the subject is susceptible to some of the other described side effects of cetuximab treatment. These include those side effects listed below.

Severe allergic reactions, with symptoms including difficulty breathing, rash, itching, low blood pressure, loss of consciousness, and heart attack have occurred in 46 of 1485 patients (3%) receiving cetuximab during clinical studies. These reactions are attributable to cetuximab infusions. Severe cases of lung disease happened in 3 of 774 patients with metastatic colorectal cancer who were given cetuximab in clinical studies. In clinical studies with cetuximab, skin problems including an acne-like rash, skin drying, cracking, redness, swelling, and abnormal hair growth were seen. The most serious side effects reported by 774 metastatic colorectal cancer patients receiving cetuximab in clinical trials were allergic reactions (3%), skin reactions (1%), serious lung disease (0.4%), fever (5%), infection (3%), kidney failure (2%), blood clots in the lung (1%), dehydration and diarrhea.

The most common side effects reported by 774 metastatic colorectal cancer patients receiving cetuximab plus Camptosar or cetuximab alone were acne-like rash (88%/90%), feeling very tired or weak (73%/48%), diarrhea (72%/25%), nausea (55%/29%), stomach pain (45%/26%), vomiting (41%/25%), fever (34%/27%), constipation (30%/26%), and headache (14%/26%).

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

A recombinant expression vector system encoding an antibody light chain, an antibody heavy chain, or both, can perform two functions in collaboration with compatible host cells. One function is to facilitate the cloning of a nucleic acid that encodes the antibody chain or chains, i e to produce usable quantities of nucleic acid (cloning vectors). The other function is to provide for replication and expression of the recombinant gene constructs in a suitable host, either by maintenance as an extrachromosomal element or by integration into the host chromosome (expression vectors). A cloning vector comprises the recombinant nucleic acid constructs as described above, an origin of replication or an autonomously replicating sequence, dominant marker sequences and, optionally, signal sequences and additional restriction sites. An expression vector additionally comprises expression control sequences essential for the transcription and translation of the recombinant nucleic acids.

In some embodiments, secretion of recombinant antibodies is directed. Signal sequences may be, for example, presequences or secretory leaders directing the secretion of the recombinant antibody, splice signals, or the like. Examples for signal sequences directing the secretion of the recombinant antibody are sequences derived from the ompA gene, the pelB (pectate lyase) gene, or the phoA gene.

Transcription of antibody sequences can be regulated by a promoter and by sequences necessary for the initiation and termination of transcription and for stabilizing the mRNA and, optionally, enhancers and further regulatory sequences. A wide variety of promoter sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of viral origin, e.g. derived from Simian virus, polyoma virus, bovine papilloma virus or Moloney sarcoma virus, or of genomic, especially murine, origin. Other vectors are suitable for both prokaryotic and eukaryotic hosts and are based on viral replication systems. Particularly preferred are vectors comprising Simian virus promoters, e.g. pSVgpt or pSVneo, further comprising an enhancer, e.g. an enhancer normally associated with the immunoglobulin gene sequences, in particular. the mouse Ig H- or L-chain enhancer.

Different approaches can be followed to obtain complete tetrameric light chain and heavy chain antibodies. In one embodiment, antibody light chains and antibody heavy chains are co-expressed in the same cells to achieve intracellular association and linkage of antibody light chains with antibody heavy chains into complete tetrameric light chain and heavy chain antibodies.

In one embodiment, a nucleic acid encoding an antibody light chain and a nucleic acid encoding an antibody heavy chain are present on two mutually compatible expression vectors which are each under the control of different or the same promoter(s). In this embodiment, the expression vectors are co-transformed or transformed individually.

In one embodiment of the invention, host cells are transformed with a recombinant rhabdovirus expression system comprising nucleic acid sequences encoding an antibody light chain and/or an antibody heavy chain of the desired recombinant antibody. Thus, in one aspect, a nucleic acid sequence can encode a single-chain recombinant antibody.

Transformation of cells of higher eukaryotic origin, such as mammalian cell lines, is achieved by methods such as infection or transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyl-dextran, dimethyl sulfoxide, glycerol or polyethylene glycol, and the like. After the transfection procedure, transfected cells are identified and selected, for example, by cultivation in a selective medium chosen depending on the nature of the selection marker, for example standard culture media such as Dulbecco's modified Eagle medium (DMEM), minimum essential medium, RPMI 1640 medium and the like, containing e.g., the corresponding antibiotic.

The present invention further encompasses methods for making and using compounds without sugars found to be able to elicit an adverse reaction. Such methods include synthesizing the compound without the sugar, using a cell line that does not add the sugar, as well as methods for removing the sugar if present using, for example, enzymes specific for that type of sugar-protein linkage.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

One type of administration encompassed by the methods of the invention is parenteral administration, which includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques Pharmaceutical compositions that are useful in the methods of the invention may be prepared, packaged, or sold in formulations suitable for oral, rectal, vaginal, parenteral, topical, pulmonary, intranasal, inhalation, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject, or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize recombinant antibodies, molecules comprising alphaGal, and practice the claimed methods. The following working examples therefore, specifically point out the preferred embodiments of the present invention, and are not to be construed as limiting in any way the remainder of the disclosure.

EXAMPLES

The rapid adverse reaction to cetuximab is characteristic of an IgE mediated response. To test this theory, serum samples, from independent centers, have been collected from patients who have or have not had an anaphylactic response to the infusion of cetuximab.

Methods

Patients and Controls

The studies reported here were approved by the Institutional Review Board at each institution. In addition to the samples from the cetuximab treated patients, samples from three distinct locations within the US were analyzed to investigate the geographical differences in the HSR rates. Detailed patient characteristics are described in Table 1. Cohort 1: Pre-treatment sera were obtained from 76 cancer patients who were treated with cetuximab. These include 35 patients enrolled between June 2005 and December 2006 at the Vanderbilt University Medical Center (VUMC) (Nashville, Tenn.); 27 patients selected from clinical trials conducted by Bristol Myers Squibb (Plainsboro, N.J.); nine ("9") patients from the Allergy and Asthma Clinic of Northwest Arkansas (Bentonville, Ark.) and 5 patients from Duke University Medical Center (Durham, N.C.). With the exception of the VUMC samples, this cohort was enriched for HSR. Cohorts 2, 3 and 4: Control sera; 2) 72 sera from healthy volunteers obtained at yearly HNSCC screening days at VUMC matched with the cancer patients at VUMC for age, sex, race and smoking history; 3) 49 patients with HNSCC presenting to Stanford University Medical Center (Menlo Park, Calif.), of whom three received cetuximab; 4) 341 sera from adult women in Boston, Mass. (15). Cohorts 3 and 4 were included as representative samples from areas where there is low prevalence (<1%) of HSR during cetuximab treatment. Six patients with recurrent anaphylaxis or angioedema presenting to the University of Virginia Allergy Clinic were also included in the study. These patients had been found to be CR-IgE(+) and their sera was used in developing the assay and evaluating specificity.

Grading of Hypersensitivity Reactions

Grading was based on documented symptoms and signs using the National Cancer Institute grading scale (NCI CTC Version 3) (16). The common characteristics of grade three reactions were skin rash, dyspnea and hypotension. Grade four is "anaphylaxis". Twenty-five of the 76 treated patients had HSR determined by the treating physicians at 15 institutions. The grading carried out by the individual investigators identified 13 mild (grade 1 or 2) and 12 severe reactions (grade 3 or 4).

Antigens Evaluated in ImmunoCAP Assays

Cetuximab and Cetuximab-Derived Antigens:

Cetuximab, which is produced by expressing clone C225 in the mouse myeloma cell line SP2/0, was provided by ImClone Systems, Incorporated (Branchburg, N.J.) (8,17). In addition, two variants of cetuximab, produced in Chinese Hamster Ovary (CHO) cell lines, were also obtained from ImClone: 1) CHO-C225, has modified glycosylation at the asparagine 88 and 299 (N88 and N229) sites as a result of its expression in CHO cells, while 2) CHO-C225-N88Q lacks glycosylation at the N88 site due to amino acid substitution (17,18). These two mAb, which were purified by the standard techniques used for cetuximab, were shown to have the same affinity for EGFR as the commercial antibody. The F(ab')2 fragment of cetuximab was prepared by digestion with pepsin and purification over a protein A column. The molecular weights of all these molecules were confirmed by SDS PAGE. Cetuximab and cetuximab-derived antigens were biotinylated using sulfosuccinimidyl 6-(biotinamido) hexanoate (EZ-Link; Pierce Biotechnology, Rockford, Il) (14).

Alternative Antigens:

Rituximab, an anti-CD20 mAb (Genentech, Inc., San Francisco, Calif.) and infliximab, an anti-TNF-alpha mAb (Centocor, Inc., Horsham, Pa.) were obtained commercially. Galactose-alpha-1,3-galactose-beta-1,4-GleNAc-beta-sp-biotin was purchased from GlycoTech Corp. (Gaithersburg, Md.). Mouse IgG was obtained from Immunology Consultants Inc. and Fel d 1 was purified by affinity chromatography using the mAb #6F9 (19).

ImmunoCAP IgE Assays

A detailed description of the ImmunoCAP assay is given elsewhere (14,20). The ImmunoCAP assay utilizes a variation of the traditional RAST in which antigens are bound to a solid phase. Serum is incubated with the solid phase and antibodies present in the sera bind to the specific antigen. Antibody-antigen complexes are detected by a secondary enzyme-labeled anti-IgE ab. Total and specific IgE antibodies were measured using both traditional ImmunoCAP (Phadia US Inc.) and the modified assay using streptavidin bound to the solid phase (14). All assays on sera from treated patients were carried out at the University of Virginia and analyzed blinded to HSR status. Cauximab was biotinylated and approximately 5 µg of biotinylated antigen was added to each streptavidin coated CAP before adding 40 µl of undiluted serum. The assays were performed with the ImmunoCAP250 instrument and the results were expressed as IU/ml where the IU both for specific and total IgE is approximately 2.4 ng. For all assays, the standard cut off for a positive reaction was 0.35 IU/ml. The Streptavidin CAP technique was also used to measure IgE ab to the variants of cetuximab, the F(ab')2 fragment, alphaGal, mouse IgG, rituximab, infliximab, and purified cat allergen Fel d 1. To investigate cross reactivity, sera were tested using commercially available CAP assays from Phadia US Inc. for IgE ab to dust mite, cat, dog, German cockroach, grass pollen, ragweed pollen, beef, pork, cows' milk and Alternaria.

Results

Serum Assays for IgE ab Cross-Reactive with Cetuximab (CR-IgE)

The assays for IgE antibodies binding to cetuximab identified positive sera with titers ranging from 0.38 to 140 IV/ml. Representative results are shown for six patients treated with cetuximab who had anaphylaxis, 11 patients who had no reaction to cetuximab, and six patients with recurrent anaphylaxis or angioedema unrelated to cetuximab treatment (Table 2). In addition to the specificity of the anti-IgE used in the assay, two lines of evidence establish that this assay was measuring IgE ab binding to cetuximab. First, a large part or all of the IgE ab was specific for the Fab part of the molecule and second, when sera were absorbed with anti-IgE, depletion of CR-IgE and total IgE occurred in parallel (Table 2).

Analysis of Pre-Existing Cetuximab-Reactive IgE Antibodies in Patients

A total of 538 serum samples were analyzed across 4 cohorts and 38 sera were positive for CR-IgE (FIG. 1). Among the 76 treated cases in cohort 1, 25 experienced HSR during the first infusion and 18/76 sera were positive for CR-IgE. Of the 18 CR-IgE(+) patients, 17 were reported by the treating physician to have had HSR, while only 8 out of 58 CR-IgE(−) patients had an HSR reported (chi-square=37.8, p<0.001). In retrospective chart review, the one patient with CR-IgE not reported to have HSR had a reaction 90 minutes after starting the infusion of cetuximab. The sensitivity and specificity of a positive IgE ab assay to predict any HSR were 68% and 98%, respectively. To predict severe HSR these values were 92% and 90%, respectively. Patients with CR-IgE had a higher rate of severe HSR compared to CR-IgE negative patients (Fisher's exact test p=0.031). Among the 8 patients who were reported to have had an HSR, but were CR-IgE negative, 7 had grade 1-2 reactions and only 1 patient had grade 3. Five of these 8 patients were rechallenged and completed treatment without further reactions. By contrast, all 18 of the patients who were subsequently found to be CR-IgE positive had had their therapy discontinued.

In control sera from Tennessee 15/72 (20.8%) were positive for CR-IgE. Both the prevalence and the titers were similar to those for the treated subjects from Tennessee (FIG. 1). Among the HNSCC sera from California and the sera from Boston, 3/49 (6.1%) and 2/341 (0.59%) were CR-IgE(+) (FIG. 1). These low rates in cohorts 3 and 4 are consistent with low rates of HSR reported in clinical trials of cetuximab in those regions of the USA.

Specificity of the IgE Antibodies that Bind to Cetuximab

Figure 2:
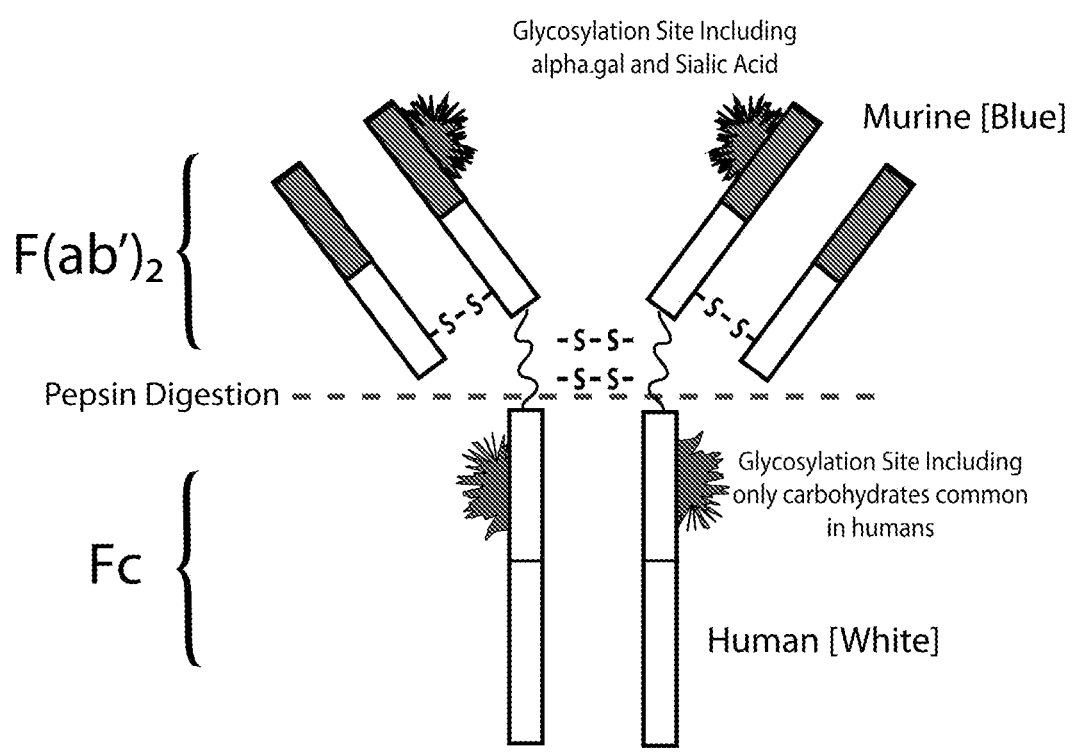
FIG. 2 is a schematic representation of the structure of cetuximab. The amino acid sequence of cetuximab has potential glycosylation sites at Asn43 of the light chain and Asn88 and Asn299 of the heavy chain. The sugars on the Fab portion include galactose-alpha-1,3-galactose (alphaGal) and the sialic acid N-glyconeurominic acid (NGNA). By contrast, glycosylation of the Fc portion of the heavy chain includes only oligosaccharides that are commonly present on human proteins.

Given that the CR-IgE antibodies were specific for the Fab portion of cetuximab, the results could be explained by IgE ab recognizing either residual mouse amino acid sequence, or the oligosaccharides on this segment of the molecule (FIG. 2). The lack of crossreactivity with other chimeric mAb (e.g. rituximab and infliximab) and the lack of CR-IgE in sera from mouse allergic subjects argue against the relevance of residual mouse amino acid sequence (Table 3 and data not shown). The Fab section of the cetuximab heavy chain is glycosylated at N88 with a range of sugars including alpha-1,3-galactose and the sialic acid N-glycolylneuraminic acid (NGNA) (17). To test whether the CR-IgE were specific for these sugars, sera were analyzed for the two differentially glycosylated variants of the antibody: CHO-C225 and CHO-C225-N88Q. We saw completely negative results with 11/11 of the cetuximab-treated CR-IgE positive sera and 5/6 of the anaphylaxis patients tested (Table 3 and data not shown). By contrast, the results for CR-IgE showed a strong positive correlation with the results for IgE ab to alphaGal, cat, dog, beef, and pork (Table 3 and data not shown). There was no significant correlation for any of the non-mammalian allergens tested (p>0.1 in each case). Although most of the CR-IgE(+) sera tested were positive for IgE ab to cat pelt, 11/12 were negative for the major cat allergen Fel d 1. Consistent with the hypothesis that the results reflect IgE ab to a common epitope, the IgE ab to cat, dog, beef and alphaGal could be fully inhibited with cetuximab (data not shown). These results are best interpreted as showing that the IgE antibodies binding to cetuximab reflect a pre-existing response to alphaGal and possibly other sugars that are present both on the Fab fragment of cetuximab and on a range of mammalian proteins.

Discussion

Although severe anaphylactic reactions have been reported following treatment with several different mAb, their mechanisms have not been defined and the reaction rates have generally been less than 1% (1-5,7,8,21). Our results show that most of the severe reactions in patients treated with cetuximab are associated with pre-existing IgE ab to alphaGal. The association with reported HSR was very strong and in keeping with that, the assay for CR-IgE identified 17 of the 21 subjects whose treatment had been discontinued after the first infusion. Unlike most other mAb, cetuximab is produced in the mouse cell line SP2/0 which expresses the gene for alpha-1,3-galactosyl transferase (17, 18). The evidence that IgE antibodies specific for the post-translational modification of a recombinant molecule can cause severe infusion reactions may have general relevance to understanding allergic responses to recombinant molecules.

In 1936, Karl Landsteiner recognized that human sera contained antibody specific for widely cross-reactive carbohydrate epitopes on mammalian proteins (22). It is now well recognized that all humans have IgG antibodies for the oligosaccharide alphaGal which is closely related to the blood group substances (23, 24). Indeed, this oligosaccharide is recognized as one of the major barriers to organ transplantation from lower mammals to baboons and this has prompted the development of a strain of pigs in which the gene for alpha-1,3-galactosyl transferase has been knocked out (23, 25).

Our finding of IgE ab to alphaGal is novel and is important for several reasons. It is obvious from our results that injecting recombinant proteins carrying this sugar can cause anaphylaxis. This finding also raises the possibility that a similar mechanism could give rise to IgE specific for the closely related blood group substances (25). Finally, wide cross-reactivity of these antibodies may put patients at risk from natural exposure to proteins carrying these sugars. The rapid reactions to cetuximab may be explained by the manner of drug treatment, i.e. intravenous injection, and also because alphaGal is present on both Fab segments of the antibody (FIG. 2), allowing for the efficient cross-linking of IgE on mast cells. Patient's who are CR-IgE(+) do not report rapid onset of allergic symptoms after the ingestion of beef, pork or cow's milk. However, we have identified a series of CR-IgE (+) patients who report episodes of anaphylaxis or severe angioedema one to three hours after eating beef or pork (Table 2 and 3). This delayed onset of symptoms could reflect the fact that the IgE is directed against a single epitope (i.e. one alphaGal moiety on each protein molecule). A similar phenomenon has been reported with IgE ab to carbohydrate epitopes of plant proteins (26, 27). In addition, it has recently been reported that some out allergic patients have IgE ab that bind to a carbohydrate epitope on cat IgA (29).

The high prevalence of HSR to cetuximab in the southeast is supported by our own data on the cohort from Tennessee and also recent publications (11). The striking difference in prevalence of CR-IgE provides a rational explanation for the difference in reaction rates between Boston or Northern California on the one hand and Tennessee, Arkansas and North Carolina on the other (6, 11, 28, 30). A high prevalence of IgE to neuromuscular blocking agents (NMBA) in Norway was found to be associated with anaphylaxis. In that case, the difference between Norway and Sweden was attributed to the use of suxamethonium, as an ingredient in a commonly used cough syrup in Norway (31, 32). The explanation for the regional distribution of CR-IgE is not clear. Our initial hypotheses included cross-reactivity with regional pollen, locally prevalent food, or a response to an infectious organism present in this area. AlphaGal is widespread on mammalian proteins and most humans have made an IgG response to the epitope (23, 24). Thus, the question should be, why do subjects in one area of the country develop IgE specific for these sugars? The effect does not appear to be a non-specific enhancement of IgE production since there was no significant association with IgE to allergens other than those derived from mammals. The regional infections that could be relevant include Histoplasmosis, a local gut pathogen such as amoeba, coccidiomycosis, *Eimeria* species or a nematode infection. Nematode infections are an interesting possibility because these pathogens are well recognized to enhance IgE and IgE ab production (33, 34). Infections with Ascaris, Strongyloides, Trichuris and Trichinella are still present in the United States although clinically important infections are rare. In support of the relevance of parasite infection, we have recently found that 80% of sera from a village in Kenya were CR-IgE(+) (unpublished data) (35). This finding may be relevant to understanding high levels of total IgE in the tropics. We hypothesize that this IgE ab response which cross-reacts with proteins from a wide range of lower mammals is a heterophile response induced by an infection that is still common in some areas of the United States.

In conclusion, we have identified pre-existing IgE ab for an oligosaccharide present on a recombinant molecule, as a novel mechanism underlying HSR. Because of the widespread use of cetuximab (and other mAb) to treat metastatic CRC or EINSCC, our evidence that an assay for IgE to cetuximab can identify patients at risk for serious HSR has significant implications for the care of cancer patients or others receiving cetuximab for any other disease or disorder. Our results may have wider implications for both evaluating the risks associated with global dissemination of antibody-based therapeutics, and understanding the relevance of an IgE response to post-translational modifications of recombinant molecules.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Edwards J C, Szczepanski L, Szechinski J, Filipowicz-Sosnowska A. et al. Efficacy of B-cell-targeted therapy with rituximab in patients with rheumatoid arthritis. N Engl J Med 2004; 350(25):2572-81.
2. Bonner J A, Harari P M, Giralt J, et al. Radiotherapy plus cetuximab for squamous-cell carcinoma of the head and neck. N Engl J Med 2006; 354(6):567-78.
3. Holgate S, Casale T, Wenzel S, et al. The anti-inflammatory effects of omalizumab confirm the central role in IgE in allergic inflammation. J Allergy Clin Immunol 2005; 115: 459-65.
4. Cheifetz A, Smedley M, Martin S, et al. The incidence and management of infusion reactions to infliximab: a large center experience. Am J Gastroenterol 2003; 98(6):1315-24.
5. Cook-Bruns N. Retrospective analysis of the safety of Herceptin immunotherapy in metastatic breast cancer Oncology 2001; 61(Suppl 2):58-66.
6. Chung K Y, Shia J, Kemeny N E, et al. Cetuximab shows activity in colorectal cancer patients with tumors that do not express the epidermal growth factor receptor by immunohistochemistry. J Clin Oncol 2005; 23(9):1803-10.
7. Omalizumab (marketed as Xolair) Information. Food and Drug Administration/Center for Drug Evaluation and Research, 2007. (Accessed Jul. 5, 2007, at http://www.fda.gov/cder/drug/infopage/omalizumab/default.htm).
8. Erbitux (Cetuximab). Drug Product Label. ImClone Systems Incorporated and Bristol-Myers Squibb Company. 2007.
9. Cunningham D, Humblet Y, Siena S, Khayat D, Bleiberg H, Santoro A, Bets D, Mueser M, Harstrick A, Verslype C, Chau I, Van Cutsem E. Cetuximab monotherapy and cetuximab plus irinotecan in irinotecan-refractory metastatic colorectal cancer. N Engl J Med 2004; 351(4):337-45.
10. Saltz L B, Meropol N J, Loehrer P J, Sr., Needle M N, Kopit J, Mayer R J. Phase II trial of cetuximab in patients with refractory colorectal cancer that expresses the epidermal growth factor receptor. J Clin Oncol 2004; 22(7):1201-8.
11. O'Neil B H, Allen R, Spigel D R, et al. High incidence of cetuximab-related infusion reactions in Tennessee and North Carolina; association with atopic history. J Clin Oncology 2007; In Press.
12. Sampson H A, Munoz-Furlong A, Bock S A, et al. Symposium on the definition and management of anaphylaxis summary report. J Allergy Clin Immunol 2005; 115:584-91.
13. Lieberman P, Kemp S, Oppenheimer J. The diagnosis and management of anaphylaxis: an updated practice primer. Joint Task Force on Practice Parameters; American Academy of Allergy, Asthma and Immunology; American College of Allergy, Asthma and Immunology; Joint Council of Allergy, Asthma and Immunology. J Allergy Clin Immunol 2005; 115:S483-S523.
14. Erwin E A, Custis N J, Satinover S M, et al. Quantitative measurement of IgE antibodies to purified allergens using streptavidin linked to a high-capacity solid phase. J Allergy Clin Immunol 2005; 115(5):1029-35.
15. Lewis S A, Weiss S T, Platts-Mills T A, et al. The role of indoor allergens sensitization and exposure in causing morbidity in women in asthma. Am J Respir Crit. Care Med 2002; 165:961-6.
16. Cancer Therapy Evaluation Program, Common Terminology Criteria for Adverse Events, Version 3.0, DCTD, NCI, NIH, DHHS Mar. 31, 2003, Publish Date: Aug. 9, 2006.
17. Qian J, Liu T, Yang L, et al. Structural characterization of N-linked oligosaccharides on monoclonal antibody cetuximab by the combination of orthogonal matrix-assisted laser desorption/ionization hybrid quadrupole-quadrepole time-of-flight tandem mass spectrometry and sequential enzymatic digestion. Analytical Biochemistry 2007; 364: 8-18.
18. Jefferis R. Glycosylation of human IgG antibodies: relevance to therapeutic applications. BioPharm 2002; 14:19-26.
19. Chapman M D, Aalberse R C, Brown M J, Platts-Mills T A. Monoclonal antibodies to the major feline allergen Fel d 1. J Immunol 1988; 140:812-8.
20. Cavalier E, Carlisi A, Chapelle J P. [Evaluation of the analytical performance of the ImmunoCap250 (Sweden Diagnostics)]. Ann Biol Clin (Paris) 2006; 64:91-4.
21. Cheifetz A, Mayer L. Monoclonal antibodies, immunogenicity, and associated infusion reactions. Mount Sinai Journal of Medicine 2005; 72:250-256.
22. Landsteiner K. The Specificity of Serological Reactions. Revised Edition. Dover Publications 1990.
23. Galili U. T alphaGal epitope and the anti-Gal antibody in xenotransplantation and in cancer immunotherapy. Immunology and Cell Biology 2005; 83:674-686.
24. Koike C, Uddin M, Wildman D, et al. Functionally important glycosyltransferase gain and loss during catarrhine primate emergence. Proc Nat Acad Sci 2007; 104(2):559-564.
25. Milland J, Sandrin M S. ABO blood group and related antigens, natural antibodies and transplantation. Tissue Antigens 2007; epublication.
26. Paschinger K, Fabini G, Schuster D, et al. Definition of immunogenic carbohydrate epitopes. Acta Biochimica Polonica 2005; 52:629-632.
27. van der Veen M J, van Ree R, Aalberse R C, Akkerdaas J, Koppelman S J, Jansen H M, van der Zee J S. Poor biologic activity of cross-reactive IgE directed to carbohydrate determinants of glycoproteins. J Allergy Clin Immunol. 1997; 100(3):327-34.
28. Timoney J, Chung K, Park V, Trocola R, Peake C, Saltz LB. Cetuximab use without chronic antihistamine premedication. Proc Am Soc Clin Oncol 2006; 24.
29. Adedoyin J, Gronlund H, Oman H, et al. Cat IgA, representative of new carbohydrate cross-reactive allergens. J Allergy Clin Immunol 2007; 119:640-5.
30. Needle M N. Safety experience with IMC-C225, an anti-epidermal growth factor receptor antibody. Semin Oncol 2002; 29(5 Supple 14):55-60.

31. Florvaag E, Johansson S G, Oman H, et al. Prevalence of IgE antibodies to morphine. Relation to the high and low incidences of NMBA anaphylaxis in Norway and Sweden, respectively. Acta Anaesthesiol Scand 2005; 49(4):437-44.
32. Johansson S G, Nopp A, Florvaag E, et al. High prevalence of IgE antibodies among blood donors in Sweden and Norway. Allergy 2005; 60(10):1312-5.
33. Mitre E, Nutman T B. IgE memory: persistence of antigen-specific IgE responses years after treatment of human filarial infections. J Allergy Clin Immunol. 2006; 117:939-45.
34. Tawill S, Le Goff L, Ali F. Both free-living and parasitic nematodes induce a characterized response that is dependent on the presence of intact glycans. Infect Immun 2004; 72:398-407.
35. Perzanowski M S, Ng'ang'a L W, Carter M C, et al. Atopy, asthma, and antibodies to Ascaris among rural and urban children in Kenya. J Pediatr 2002; 140:582-8.

TABLE 1

Characteristics of study cohorts

|  | Cohort 1 | | Cohort 2 | Cohort 3 | Cohort 4 | |
| --- | --- | --- | --- | --- | --- | --- |
|  | Tennessee Cases (N = 35) | Other Cases (N = 41) | Tennessee Controls (N = 72) | California Controls (N = 49) | Boston Controls (N = 341) | Summary |
| Age |  |  |  |  |  |  |
| Median (range) | 58 (43-93) | 63 (41-81) | 58 (32-82) | 58 (36-97) | N/A | 58 (32-97) |
| Sex |  |  |  |  |  | N = 538 |
| Male/Female | 22/13 | 22/19 | 40/32 | 37/12 | 0/341 | 121/417 |
| % Male | 63 | 54 | 56 | 76 | 0 | 22 |
| Race |  |  |  |  |  | N = 538 |
| White | 33 | 35 | 65 | 23 | 236 | 73% |
| Black | 2 | 5 | 7 | 2 | 54 | 3% |
| Other | 0 | 1 | 0 | 2 | 32 | 1% |
| Unknown | 0 | 0 | 0 | 22 | 19 | 24% |
| Tobacco use |  |  |  |  |  | N = 197 |
| Current | 18 | 14 | 16 | 0 |  | 24% |
| Former | 3 | 11 | 25 | 0 | N/A | 20% |
| Never | 13 | 16 | 31 | 0 |  | 30% |
| Unknown | 1 | 0 | 0 | 49 |  | 25% |
| Tumor site |  |  |  |  |  | N = 125 |
| Head and Neck | 18 | 5 |  | 49 |  | 58% |
| Colorectal | 17 | 35 | N/A | 0 | N/A | 42% |
| Lung | 0 | 1 |  | 0 |  | 1% |
| Clinical Stage |  |  |  |  |  | N = 76 |
| I-II | 9 | 4 |  |  |  | 17% |
| III | 8 | 6 | N/A | N/A | N/A | 18% |
| IV | 14 | 25 |  |  |  | 51% |
| Unknown | 4 | 6 |  |  |  | 13% |
| Investigator HSR |  |  |  |  |  | N = 26 |
| Low grade | 6 | 7 |  |  |  | 50% |
| High grade | 4 | 8 | N/A | N/A | N/A | 46% |
| Late response | 1 | 0 |  |  |  | 4% |
| Retrospective HSR[1] |  |  |  |  |  | N = 26 |
| Low grade | 0 | 2 | N/A | N/A | N/A | 8% |
| High grade | 11 | 13 |  |  |  | 92% |

N/A = Not Available
[1]Scoring based on blind analysis of case reports

TABLE 2

IgE antibodies (IU/mL) to Cetuximab and the F(ab')2 fragment of the molecule.

|  |  |  |  |  |  | Depletion with anti-IgE[1]: | |
| --- | --- | --- | --- | --- | --- | --- | --- |
| Hypersensitivity Reaction |  | Total IgE | Cetuximab[2] | F(ab')2 Fragment[2] | Rituximab[2] | Total IgE % Remaining | CR-IgE % Remaining[2] |
| Anaphylaxis with Cetuximab | 1[3] | 3161 | 41.6 | 40.9 | 0.35 | 1.3 | 1.0 |
|  | 2 | 887 | 38.8 | 52.3 | 0.35 | 8.9 | 12 |
|  | 3[3] | 374 | 20.2 | 26 | 0.35 | 3.4 | 3.2 |
|  | 4[3] | 348 | 11.1 | 13.2 | 0.35 | 9.1 | 5.2 |
|  | 5 | 58.5 | 4.9 | 5.7 | 0.35 | 29 | 21 |
|  | 6[3] | 22.2 | 4.2 | 6.6 | 0.35 | 15 | 8.4 |
| Recurrent Anaphylaxis[4] | 7 | 1081 | 131 | 158 | 1.75 | 4.9 | 4.0 |
|  | 8 | 243 | 69.2 | 86.8 | 0.35 | 0.9 | 4.0 |
|  | 9 | 242 | 55.1 | 99.6 | 0.35 | 9.6 | 6.7 |
|  | 10 | 188 | 43.5 | 45.8 | 0.35 | 11.1 | 5.9 |
|  | 11 | 538 | 81.1 | 100 | 0.35 | 1.4 | 5.7 |
|  | 12 | 63.6 | 13 | 17.9 | 0.35 | 11 | 4.9 |

TABLE 2-continued

IgE antibodies (IU/mL) to Cetuximab and the F(ab')2 fragment of the molecule.

| | | | | | Depletion with anti-IgE[1]: | |
|---|---|---|---|---|---|---|
| Hypersensitivity Reaction | Total IgE | Cetuximab[2] | F(ab')2 Fragment[2] | Rituximab[2] | Total IgE % Remaining | CR-IgE % Remaining[2] |
| HSR, N = 12 # Positive/total # (mean)[5] | 315 (130-760)[6] | 12/12 (26.7) | 12/12 (33.4) | 1/12 (—) | 5.7[7] | 5.3[7] |
| Non-HSR, N = 11 # Positive/total #[8] | 17.4 (6.8-45)[6] | 0/11 | 0/11 | 0/11 | ND | ND |

ND = not determined
Footnotes for Table 2:
[1]Omaluzimab (monoclonal anti-IgE) bound to protein A agarose beads was incubated overnight at 4 degrees C. at a 1:5 bead to serum volume ratio.
[2]Assayed with biotinylated antigen on streptavidin CAP.
[3]Patients with grade 4 anaphylaxis
[4]Patients presenting to the University of Virginia Allergic Disease Clinic with recurrent angioedema or anaphylaxis found to be CR-IgE(+). Patients 11 and 12 reported severe episodes of angioedema.
[5]Summary of patients 1-12.
[6]Geometric mean (±95% confidence interval)
[6]Mean percent remaining after depletion
[7]Summary of 11 cetuximab-treated cancer patients where no HSR was reported.

TABLE 3

Specificity of the IgE antibodies (IU/mL) that cross-react with the monoclonal antibody cetuximab

| | | Cells lines used to express cetuximab: | | | | | | |
|---|---|---|---|---|---|---|---|---|
| Hypersensitivity Reaction | | SP2/0 (Mouse)[1] | CHO[1] | AlphaGal[1,2] | Mouse IgG[1] | Cat | Dog | Fel d 1[1] | Beef |
| Anaphylaxis with Cetuximab | 1 | 41.6 | 0.35 | 13.8 | 0.35 | 3.16 | 2.6 | 0.35 | 3.02 |
| | 2 | 38.8 | 0.35 | 35.2 | 0.35 | 13.2 | 12.3 | 0.35 | 12.46 |
| | 3 | 20.2 | 0.35 | 12.6 | 0.35 | 9.34 | 9.77 | 0.35 | 6.92 |
| | 4 | 11.1 | 0.35 | 2.91 | 0.35 | 1.94 | 1.86 | 0.35 | 1.82 |
| | 5 | 4.86 | 0.35 | 2.02 | 0.35 | 0.35 | 0.35 | 0.35 | 0.35 |
| | 6 | 4.15 | 0.35 | 2.71 | 0.35 | 1.54 | 1.5 | 0.35 | 1.66 |
| Recurrent Anaphylaxis[3] | 7 | 131 | 1.89 | 38.9 | 1.75 | 41.5 | 34.5 | 3.64 | 32.9 |
| | 8 | 69.2 | 0.35 | 42.1 | 1.19 | 27.7 | 32 | 0.35 | 26.2 |
| | 9 | 55.1 | 0.35 | 32.2 | 0.43 | 22.2 | 25.1 | 0.35 | 13.8 |
| | 10 | 43.5 | 0.35 | 32.3 | 0.35 | 37.3 | 29.4 | 0.35 | 3.48 |
| | 11 | 81.1 | 0.35 | 100 | 0.35 | 14.3 | 14.7 | 0.35 | 8.75 |
| | 12 | 13 | 0.35 | 9.03 | 0.78 | 8.86 | 8.84 | 0.35 | 8.9 |
| HSR, N = 12 # Positive/total # (mean)[4] | | 12/12 (27.7) | 1/12 (—) | 12/12 (25.5) | 4/12 (—) | 11/12 (10.3) | 11/12 (9.93) | 1/12 (—) | 11/12 (7.16) |
| Non-HSR, N = 11 # Positive/total #[5] | | 0/11 | 0/11 | 0/11 | 0/11 | 0/11[6] | 0/11[6] | 0/11 | 0/11[6] |

Footnotes for Table 3:
[1]Assayed with biotinylated antigen on streptavidin CAP.
[2]galactose-alpha1,3-galactose-beta1,4GlcNAcbeta-sp-biotin
[3]Patients presenting to the University of Virginia Allergic Disease clinic with recurrent angioedema or anaphylaxis found to be CR-IgE positive. Patients 7-10 reported episodes of anaphylaxis.
[4]Summary of patients 1-12.
[5]Summary of 11 cetuximab-treated patients without HSR.
[6]chi-square = 19.3; p < 0.001, when compared to anaphylaxis patients.

What is claimed is:

1. A method of identifying whether a compound comprises the oligosaccharide moiety galactose-alpha-1,3-galactose, said method comprising:
   combining the compound with an IgE antibody which binds specifically to galactose-alpha-1,3-galactose to form a complex comprising the galactose-alpha-1,3-galactose of the compound bound specifically IgE antibody; and
   detecting the presence of the complex, wherein the presence of the complex indicates that the compound comprises the oligosaccharide moiety galactose-alpha-1,3-galactose.

2. A method of screening a sample, for the presence or amount of IgE antibodies specific for alphaGal, comprising;
   (a) contacting the sample with a known amount of an isolated compound comprising the moiety galactose-alpha-1,3-galatose (alphaGal) that specifically binds to said IgE antibodies in the sample, so as to form complexes between alphaGal moieties on said compound and said IgE antibodies; and
   (b) detecting the presence or amount of said complexes, wherein the presence or amount indicates that the sample comprises said IgE antibodies.

3. The method of claim 2 wherein the presence or amount of IgE is detected by reacting the complex with a secondary enzyme-labeled anti-IgE antibody.

4. The method of claim 2, wherein the sample is screened for the presence of IgE antibodies specific for alphaGal.

5. The method of claim 2, wherein the sample is screened for the amount of IgE antibodies specific for alphaGal.

6. The method of claim 2, wherein said biological sample is selected from the group consisting of blood, serum, and plasma.

7. The method of claim 2, wherein said sample is a human sample.

8. The method of claim 1 or 2, wherein said compound is a protein.

9. The method of claim 8, wherein said protein is an antibody.

10. The method of claim 9, wherein said antibody is a therapeutic antibody.

11. The method of claim 2, wherein said IgE antibody cross-reacts with alphaGal moieties on cetuximab or on the $F(ab')_2$ fragment cetuximab.

12. The method of claim 11, wherein said IgE antibody which forms complexes with alphaGal moieties is measured using an ImmunoCAP assay.

13. The method of claim 12, wherein said ImmunoCAP assay is a modified ImmunoCAP) assay using streptavidin bound to the solid phase.

14. The method of claim 13, wherein the level of said IgE is expressed in IU/ml.

* * * * *